United States Patent [19]

Siu

[11] 4,190,660
[45] Feb. 26, 1980

[54] ANTI-DRUG WITHDRAWAL SYNDROME COMPOSITION AND METHOD OF USE

[76] Inventor: Patrick M. Siu, 103 Sheffield St., Silver Spring, Md. 20910

[21] Appl. No.: 932,940

[22] Filed: Aug. 11, 1978

[51] Int. Cl.$^2$ ............................................. A61K 31/47
[52] U.S. Cl. .................................... 424/258; 546/139; 546/143; 546/144
[58] Field of Search ................. 424/258; 260/288 CE; 546/139, 143, 144

[56] References Cited

U.S. PATENT DOCUMENTS

| | | | |
|---|---|---|---|
| 3,595,864 | 7/1971 | Seeger et al. | 260/286 |
| 3,885,027 | 5/1975 | Shaw et al. | 424/44 |

OTHER PUBLICATIONS

Journal of American Chemical Society, 47, 414–416, (1952).
Surrey, A. R., Name Reactions in Organic Chemistry, Academic Press, New York, N. Y., pp. 190–191, (1961).
Remick, Electronic Interpretations of Organic Chemistry, (1949), 2nd. ed., pp. 50–56, 103, 104.
Martin, et al., Psychopharmacologia, 4, 247–260, (1963).
Goodman & Gilman, Pharm. Basis of Therapeutics, 4th. ed. (1963), pp. 247–260.
Chemical Abstracts, 73:109646y (1970).
Goth, Medical Pharmacology, 3rd ed., (1966), pp. 275–289.

Primary Examiner—Leonard Schenkman
Attorney, Agent, or Firm—James F. Jones

[57] ABSTRACT

A compound of the following formula

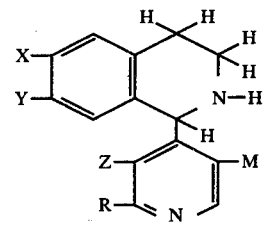

wherein:
X is H, OH, or halogen group;
Y is OH, amino or halogen group;
Z is OH, amino or halogen group;
M is $CH_2OH$, $CH_2PO_4$, $CH_2Cl$, $CH_2Br$, $CH_2Fl$, or $CH_2I$ group, and
R is $H_2$ or an alkyl group having 1 to 5 carbon atoms, when employed in pharmaceutically acceptable quantities alleviate the drug withdrawal syndrome from drug dependent warm blooded animals. A particular compound found suitable for this purpose is 1-(2-methyl-3-hydroxy-5-hydroxymethyl-4-pyridyl)-6,7-dihydroxy-1,2,3,4-tetrahydroisoquinoline.

4 Claims, No Drawings

ANTI-DRUG WITHDRAWAL SYNDROME COMPOSITION AND METHOD OF USE

BACKGROUND OF THE INVENTION

A major problem existing in society today is the widespread usage by a great many individuals of addictive drugs, such as, for example, morphine, heroin, and the like, and the resulting problems created by such usage. Most drug dependent individuals seek to endeavor to break the use of the drugs after a period of additiction but find it extremely difficult to do so. For example, siome individuals seek to stop the use of the drug completely. However, such a procedure is virtually impossible without the individual being hospitalized and undergoing a carefully controlled and monitored hospitalized tretment. Even under such a treatment, the individual suffers severe withdrawal symptons that oftentimes have a deleterious effect on the health of the individual.

Another procedure that has been employed extensively in aiding the withdrawal of an individual from certain addictive drugs is the so-called Methadone treatment. In such a procedure, the drug addicted individual is given periodic dosages of Methadone as a substitute for the addictive drug. While this treatment may result in a withdrawal from dependence on the addictive drug, Methadone in itself is addictive. Thus, this procedure, in effect, results in substituting one drug for another rather than a complete withdrawal from a drug dependence.

SUMMARY OF THE INVENTION

The present invention relates to the compositions for and the method of treating human beings to alleviate and minimize the withdrawal syndrome from drug dependent humans undergoing withdrawal treatment. More particularly, the present invention relates to a method of treatment of drug dependent individuals with substitution products of isoquinoline derivatives to minimize problems created during the withdrawal procedure from drug addiction.

In accordance with the present invention, it has been found that when an individual or patient is undergoing a withdrawal from harmful addictive drugs, the withdrawal syndrome created by the complete abstinence from the drug can be material minimized by giving the patient a pharmacologically acceptable dosage of certain substitution products of particular isoquinoline derivatives. By the use of these particular isoquinoline materials on a controlled basis, the patient is not subjected to the withdrawal syndromes he would normally encounter. Thus, the present invention provides a treatment making it far easier for a drug dependent individual to rid himself of the drug addiction than heretofore possible.

The isoquinoline derivatives that have been found to possess the property of alleviating and minimizing the drug withdrawal syndrome possess the following general formula:

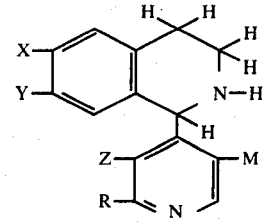

wherein:
X is H, OH, or halogen group;
Y is OH, amino or halogen group;
Z is OH, amino or halogen group;
M is $CH_2OH$, $CH_2PO_4$, $CH_2Cl$, $CH_2Br$, $CH_2Fl$, or $CH_2I$ group, and
R is $H_2$ or an alkyl group having 1 to 5 carbon atoms. when employed in pharmaceutically acceptable quantities alleviate the drug withdrawal syndrome from drug dependent warm blooded animals. A particular compound found suitable for this purpose is 1-(2-methyl-3-hydroxy-5-hydroxymethyl-4-pyridyl)-6,7-dihydroxy-1,2,3,4-tetrahydroisoquinoline.

A particular isoquinoline derivative within the foregoing general formula that has been found to be of particular utility in the suppressing of the withdrawal syndrome effect created during the drug withdrawal treatment is 1-(2-methyl-3-hydroxy-5-hydroxymethyl-4-pyridyl)-6,7-dihydroxy-1,2,3,4-tetrahydroisoquinoline having the following formula:

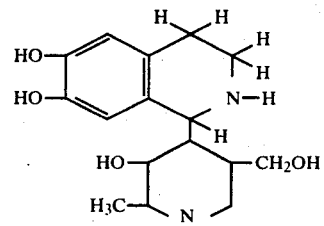

The above compound may be prepared by combining pyridoxal and 3,4-dihydroxyphenylethylamine in the presence of water at room temperature. The resulting condensation product is precipitated from the formed solution by adjusting the reaction mixture with a suitable reagent so that the pH value of the solution will be from neutral to an alkaline pH. The resulting solution is filtered, with the formed precipitate being filtered from the solution. The resulting precipitate in the form of a colorless compound is thereafter washed with old distilled water. The washed filtered precipitate is dissolve in hot dimethylsulfoxide with the resulting material being thereafter permitted to cool to room temperature. The cooling may be accomplished, if desired, by means of an ice bath, or, in the alternative, be permitted to cool by standing. The formed compound is crystallized from the dimethylsulfoxide solvent in the form of colorless crystals and washed with cold distilled water. The compound thus is in the form of colorless crystal monohydrate.

The formed compound was found to have an $R_f$ value of 0.17 when chromatographed on TLC silica gel F-254 plates ascending at room temperature for 9 hours using n-butanol saturated with 1 N HCl as the developing solvent and an $R_f$ value of 0.12 when chromatographed on Whatman No. 1 filtered paper for 18 hours at room temperature using n-butanol saturated with 1 N HCl as the developing solvent. The compound was found to absorb ultraviolet light and found to possess a decomposition range of 210° to 220° C.

The compound was subjected to chemical elemental analysis for carbon, hydrogen and nitrogen, and found to give similar values between those found and those calculated for the monohydrate form of the compound. The empirical formula based on the chemical elemental analysis is $C_{16}H_{20}O_5N_2$ or $C_{16}H_{18}O_4N_2 \cdot H_2O$ corresponding to a molecular weight of 320.

The compound was subjected to chemical ionization in a Finnegan 3100D Mass Spectrometer and was found to give major peaks at 303 and 285. The peak at 303 indicates a molecular weight of 302 for the anhydrous form of the compound. The peak at 285 represents an ionic species of the parent compound resulting from the loss of a molecule of water.

The compound was also subjected to a (NMR) Spectroscopy in a Varian Model T60-A NMR Spectrometer using tetramethylsilane as the standard in dimethylsulfoxide (DMSO) solvent and was found to give peaks at $\delta$ positions 2.9, 4.9, 6.35, 6.5, 6.9, and 8.4 corresponding to magnetic resonance of hydrogens at pyridoxine-2-methyl, pyridoxine-5-$CH_2OH$, isoquinoline-5H, isoquinoline-1-methine, isoquinoline-8H, and pyridoxine-6H, respectively.

The compound of the present invention when employed in pharmaceutically acceptable amounts to control or minimize the drug withdrawal syndrome in the patient has been found to be non-toxic and possesses no known deleterious side effects. The compound of the present invention may be incorporated in any suitable manner with an acceptable pharamceutical carrier for administration to the patient. The compound may be administered orally in the form of a suspension, elixir, packaged powder, capsule, pill, tablet, lozenge, and the like, or it may be used parentally by intramuscular injection. The pharmaceutical vehicle carriers to be employed with the compound of the present invention to produce the desired pharmaceutical composition may be any inert or excipient material normally employed as pharmaceutical composition components, such as, for example, binders, fillers, lubricants, stabilizers, preservants, retardants, buffers, colors, etc. Examples of such materials are cellulose derivatives, such as, for example, microcrystalline cellulose, carboxymethyl cellulose, etc.; starches, such as, for example, potato, maize, wheat, arrowroot, amylopectine, etc.; sugars, such as, for example, lactose, sucrose, saccharose, and other ingredients, such as, for example, gelatine, calcium phosphates, stearic acid powder, talc, mannitol, sorbitol, calcium stearate, magnesium stearate, polyethylene glycols, agar, gum acacia, etc.

The dosage of the anti-withdrawal syndrome compound of the present invention in each case may vary. In general, dosages normally employed in formulating pharmaceutical compositions will be, for example, on the order of 10 to 2000 mg. However, the exact individual dosage as well as daily dosage in a particular case will, of course, be determined according to established medical principles under the direction of a physician.

In the use of the compound of the present invention by way of a pill or tablet, such use will range in size from 200 to 600 mg., with the usual size of the tablet being on the order of 400 to 500 mg. In this form of use, the compound will be combined in a conventional manner with the excipient or inert ingredients, such as the lubricants, binders, fillers, and the like, of the type hereinbefore indicated in any suitable and well known manner to form a free-flowing granulation of the carrier material and the active ingredient in proper dosage form. The granular mixture will thereafter be fed to a tablet forming machine where tablets containing the individual dosage units of the anti-withdrawal syndrome compound thereafter are pressed or punched. In the administration orally of the active ingredient of the present invention in unit dosage form by way of tablet, the compound may be present in 0.1 to 1 gram per tablet, and preferably from 0.5 to 250 grams per tablet. If desired, the tablet may be given a sugar or lacquer coating.

The active ingredient of the present invention can be formulated also in capsule form and used in this manner as an anti-drug withdrawal syndrome compound. The general procedure for this form of use is to combine the therapeutic agent with the excipient ingredients in a conventional manner to produce a complete mixture of the therapeutic agent and the carrier components. Such a mixture is thereafter placed in a conventional manner in individual capsule units to produce an individual dosage. The unit dosage for use of the composition in capsule form may correspond in general with the unit dosage employed in the tablet form but may be of a lesser mg. weight in many instances.

In parental use, the active ingredient of the present invention may be suspended or partially dissolved in a conventional saline solution or like carrier and thereafter injected in proper dosage form. In general, the dosage will be about 0.2 to 5% by wt. in an acidified aqueous suspension, and such suspension, if desired, may contain buffers or stabilizing agents. Such parental use will, in general, be by intramuscular injection.

DESCRIPTION OF SPECIFIC AND ILLUSTRATIVE EMBODIMENTS

In other to further illustrate the present invention, reference is to be had to the following examples:

Preparation of
1-(2-Methyl-3-Hydroxy-5-Hydroxymethyl-4-Pyridyl)-6,7-Dihydroxy-1,2,3,4-Tetrahydroisoquinoline

EXAMPLE A

A solution containing 5 grams of pyridoxal hydrochloride in 200 cc of distilled water is combined with a 200 cc solution containing 5 grams of 3,4-dihydroxyphenylethylamine (dopamine) hydrochloride. The mixture was adjusted to pH thereof to an approximate value of 7.0 with a pH meter by slow addition of 50 cc of 1.0 N NaOH with constant stirring to effect a precipitation of the formed condensate from the solution. The condensation product was thereafter filtered or centrifuged in the cold and 4.4 grams of a colorless condensate product was recovered.

The total amount of the dried condensation product was dissolved in 55 cc of dimethylsulfoxide heated to a temperature of 53° C. The solution was placed in an ice bath and permitted to cool. A separation of the condensation product from solution results and further separation occurred with the addition of 60 cc of cold distilled water. The solution after being cooled was filtered, washed with cold distilled water and dried in vacuo over $P_2O_5$, resulting in the production of approximately 4 grams of a condensation product identified as 1-(2- methyl-3-hydroxymethyl-4-pyridyl)-6,7-dihydroxy-1,2,3,4-tetrahydroisoquinoline.

In order to further illustrate the present invention, the following examples of pharmaceutical compositions made in accordance with the present invention and found to minimize the effect of the drug withdrawal syndrome are given. In the following examples the active ingredient of the present invention will be identified, for the sake of brevity, by the term "A.W.S.P.", which denotes the anti-withdrawal syndrome product identified as 1-(2-methyl-3-hydroxy-5-hydroxymethyl-4-pyridyl)-6,7-dihydroxy-1,2,3,4-tetrahydroisoquinoline:

|  | Mg/tablet |
|---|---|
| Calcium phosphate | 160 |
| Lactose powder | 365 |
| Magnesium Stearate | 5 |
| A.W.S.P. | 300 |
|  | 830 mg. |

The above ingredients are granulated and mixed with one another in a conventional and known pharmaceutical technique to produce a free-flowing granulation of the component parts. The granulated mixture is then compressed in a conventional tablet forming machine into 480 mg. tablets.

EXAMPLE 2

|  | Mg/capsule |
|---|---|
| Microcrystalline cellulose* | 200 |
| Lactose powder | 100 |
| Carboxymethyl cellulose | 20 |
| A.W.S.P. | 500 |
|  | 820 mg. |

*Marketed under the trademark "Avicel" by american Viscose Corp., Marcus Hook, Pa.

The above named ingredients are blended with one another in a known pharmaceutical technique to produce a thorough mixture of the ingredients. Thereafter the mixture is placed in a No. 2 hard gelatin capsule and is ready for use in this manner.

EXAMPLE 3

|  | Gram |
|---|---|
| A.W.S.P. | 2.5 |
| Sodium chloride | 0.5 |
| Pyrogen free distilled water** q.s. | 100 |

**Acidified to pH 4.5

The A.W.S.P. is dissolved to the extent possible under aseptic conditions in the pyrogen free acidified distilled water. The sodium chloride was then added to render the solution substantially isotonic. The solution so formed is then filled into ampules having a normal 2 ml. capacity in an amount of 2.2 ml. per ampule. The ampule is thereafter sealed and sterilized by heating it in an autoclave at about 115° C. for 30 minutes. The ampule is ready for intramuscular injection.

TEST DATA

To illustrate the alleviating effect of the compound of the present invention on the drug withdrawal syndrome, reference is to be had to the followng test data:

Sprague-Dawley male rats weighing approximately 250 grams were made morphine-dependent by subcutaneous implantation of morphine alkaloid pellets and the withdrawal syndrome was precipitated by intramuscular injection of naloxone hydrochloride. The withdrawal syndrome is determined by the number of body shake episodes that occurred within the first 10 minutes after the naloxone hydrochloride injection.

| Exp.[a] | Group[b] | Treatment[c] | Mean±SEM[d] | Range | Median |
|---|---|---|---|---|---|
| I | A | Saline, morphine | 7.8±1.1 | 5–10 | 8 |
|  | B | P, morphine | 3.3±0.8 | 1–4 | 4 |
|  | C | P, placebo | 0 | 0 | 0 |
| II | D | Saline, morphine | 4.0±1.4 | 0–10 | 2.5 |
|  | E | P, morphine | 0.3±0.2 | 0–1 | 0 |

P=Condensation product of present invention.
[a]Exp.I was performed during the Winter month and Exp. II during the late Spring month.
[b]Groups A, B and C consisted of 4 rats per group; and Groups D and E consisted of a total of 8 rats per group resulting from the combination of two separate experiments of 4 rats per group per experiment. Each rat in Groups B and C received ip injections of 14.6 mg of the condensation product on days 1, 2, 4, and 7 and Group A as the controls with saline on corresponding days. The injection of the condensation product on Day-7 into each rat in Groups B and C was made 5 hours before the naloxone hydrochloride injection. Each rat in Group E received a single ip injection of 14.6 mg of the condensation product on Day-7, two and one-half hours before naloxone hydrochloride injection. Group D is the control group in Experiment II.
[c]Morphine alkaloid and placebo pellets were implanted subcutaneously on Day-4; naloxone hydrochloride (0.40 mg per rat) by im injection on Day-7.
[d]The mean value represents the number of convulsive body shake episodes in the morphine-dependent rats after the naloxone hydrochloride injection. Statistical analysis gave a Chi Square value of 7.24 in Experiment I and a p=0.027 value. A Mann-Whitney one-tailed U-test gave significant difference between Group A and Group B at p=0.01 (U=0) in Experiment I, and between Group D and Group E at p=0.01 (U=7) in Experiment II.

The data show that morphine-dependent rats given 1-(2-methyl-3-hydroxy-5-hydroxymethyl-4-pyridyl)-6,7-dihydroxy-1,2,3,4-tetrahydroisoquinoline (condensation product) had fewer body shake episodes during naloxone-induced withdrawal than similarly dependent rats given saline alone. The compound is effective with only a single injection, as shown in Experiment II.

TOXICOLOGICAL TEST DATA

To determine the toxicity of 1-(2-methyl-3-hydroxy-5-hydroxymethyl-4-pyridyl)-6,7-dihydroxy-1,2,3,4-tetrahydroiso-quinoline (condensation product) when employed as a pharmaceutical composition, the condensation product was tested on rats to determine the approximate lethal dose (ALD) determination by intraperitoneal injection and by oral administration. The tests were as follows:

INTRAPERITONEAL INJECTION

White ICR albino male mice weighing approximately 20 g were given the condensation product of the present invention by intraperitoneal injection as single doses at 0, 300, 450, 680, 1,000, 1,500, and 2,250 mg/kg body weight, respectively. The mice were observed during the next 14 days for general appearances in skin tone, fur condition, alertness and behavioral abnormalities. The body weights were recorded each day. During this period no deaths occurred. The mice appeared healthy with normal behavior, the fur was smooth and shiny, and the skin color was pink. The weight gains were similar among all the mice. The approximate lethal dose determined by the procedure is greater than 2,250 mg/kg body weight in male mice.

ORAL ADMINISTRATION

White ICR albino male mice weighing approximately 20 g were starved for 24 hours and given water ad libidum. The condensation product of the present invention was given by stomach tube as single doses at 0,680, 1,500 2,250, and 3,000 mg/kg body weight, respectively. The mice were observed during the next 14 days for general appearances in skin tone, fur condition, alertness and behavioral abnormalities. The body weights were recorded each day. Two deaths occurred due to improper intubation technique employed. The mouse given 3,000 mg/kg of the test substance die during the intubation process. The mouse at the 1,500 mg/kg level appeared weak and moribund soon after the intubation process and finally died within 2 hours. The mice at the 0,680, and 2,250 mg/kg dose level, however, survived. They appeared healthy and alert with pink skin, smooth fur, and normal behavior. Their body weight gains were similar. The approximate lethal dose determination by the oral route is greater than 2,250 mg/kg body weight in male mice.

While there have been described herein what are at present considered preferred embodiments of the invention. It will be obvious to those skilled in the art that modifications and changes may be made therein without departing from the essence of the invention. It is therefore to be understood that the exemplary embodiments are illustrative and not restrictive of the invention, the scope of which is defined in the appended claims, and that all modifications that come within the meaning and range of equivalency of the claims are intended to be included therein.

I claim:

1. A pharmaceutical composition in dosage unit for alleviating the withdrawal syndrome created in an individual undergoing drug withdrawal comprising a dosage unit in the form of a powder, tablet, capsule or sterile isotonic solution for injection containing an effective but non-toxic quantity in a pharmaceutically acceptable carrier of a compound having the following general formula:

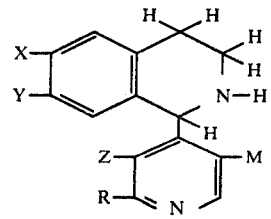

ps wherein:
X is H, OH, or halogen group;
Y is OH, amino or halogen group;
Z is OH, amino or halogen group;
M is $CH_2OH$, $CH_2PO_4$, $CH_2Cl$, $CH_2Br$, $Ch_2Fl$, or $CH_2l$ group,
R is $H_2$ or an alkyl group having 1 to 5 carbon atoms.

2. A pharmaceutical composition in accordance with claim 1, wherein the compound is 1-(2-methyl-3-hydroxy-5-hydroxymethyl-4-pyridyl)-6,7-dihydroxy-1,2,3,4-tetrahydroisoquinoline.

3. A method for alleviating the withdrawal syndrome from a drug dependent individual undergoing drug withdrawal comprising giving the individual a pharmaceutically acceptable dosage unit form of the pharmaceutical composition of claim 1 having the following general formula:

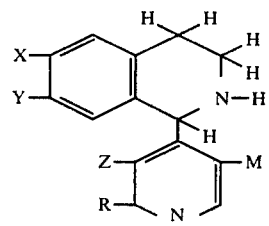

wherein:
X is H, OH, or halogen group;
Y is OH, amine or halogen group;
Z is OH, amino or halogen group;
M is $CH_2OH$, $CH_2PO_4$, $CH_2Cl$, $CH_2Br$, $CH_2Fl$, or $CH_2l$ group, and
R is $H_2$ is an alkyl group having 1 to 5 carbon atoms.

4. A method for alleviating the withdrawal syndrome in accordance with claim 3, wherein the pharmaceutical composition is the pharmaceutical composition of claim 2.

* * * * *